US012568871B2

(12) United States Patent
Schroeder et al.

(10) Patent No.: US 12,568,871 B2
(45) Date of Patent: Mar. 10, 2026

(54) SYSTEM AND METHOD FOR DETERMINING RESIDUE COVERAGE OF A FIELD

(71) Applicant: CNH Industrial America LLC, New Holland, PA (US)

(72) Inventors: Brittany Schroeder, Bunker Hill, IN (US); Joshua D. Knoblauch, Lowpoint, IL (US)

(73) Assignee: CNH Industrial America LLC, New Holland, PA (US)

( * ) Notice: Subject to any disclaimer, the term of this patent is extended or adjusted under 35 U.S.C. 154(b) by 400 days.

(21) Appl. No.: 18/450,464

(22) Filed: Aug. 16, 2023

(65) Prior Publication Data

US 2025/0057066 A1    Feb. 20, 2025

(51) Int. Cl.
  *A01B 76/00*     (2006.01)
  *G01N 33/24*     (2006.01)
  *G01S 17/88*     (2006.01)
(52) U.S. Cl.
  CPC ........... *A01B 76/00* (2013.01); *G01N 33/246* (2013.01); *G01S 17/88* (2013.01)
(58) Field of Classification Search
  CPC ...... A01B 76/00; A01B 47/00; G01N 33/246; G01N 33/245; G01S 17/88
  USPC .......................................................... 172/1
  See application file for complete search history.

(56) References Cited

U.S. PATENT DOCUMENTS

| | | | |
|---|---|---|---|
| 11,262,344 B2 * | 3/2022 | Schoeny | ................ A01C 7/205 |
| 11,622,494 B2 | 4/2023 | Arnett et al. | |
| 2020/0113113 A1 * | 4/2020 | Shearer | ................ A01B 49/027 |
| 2020/0120854 A1 * | 4/2020 | Shearer | .................. A01B 63/32 |
| 2020/0187408 A1 * | 6/2020 | Forbes | ................ A01B 79/005 |
| 2020/0236836 A1 * | 7/2020 | Barrick | ................ A01B 79/005 |
| 2022/0210975 A1 * | 7/2022 | Digman | .................. A01F 15/00 |
| 2022/0279697 A1 | 9/2022 | Johnson et al. | |
| 2023/0255132 A1 * | 8/2023 | Nadke | .................. G05D 1/0278 |
| | | | 701/50 |

* cited by examiner

*Primary Examiner* — Muhammad Shafi
(74) *Attorney, Agent, or Firm* — Dority & Manning, P.A.

(57)            ABSTRACT

A system for determining residue coverage of a field includes a LiDAR sensor configured to emit light-based output signals for reflection off of a field surface of a portion of a field and detect reflections of the light-based output signals as return signals. Furthermore, the system includes a soil moisture sensor configured to generate soil moisture sensor data indicative of a soil moisture content of the portion of the field. Additionally, a computing system is configured to receive LiDAR sensor data associated with the return signals detected by the LiDAR sensor. Moreover, the computing system is configured to determine a soil moisture value for the portion of the field based on the soil moisture sensor data. In addition, the computing system is configured to determine a residue coverage value of the portion of the field based on the determined soil moisture value and the LiDAR sensor data.

17 Claims, 6 Drawing Sheets

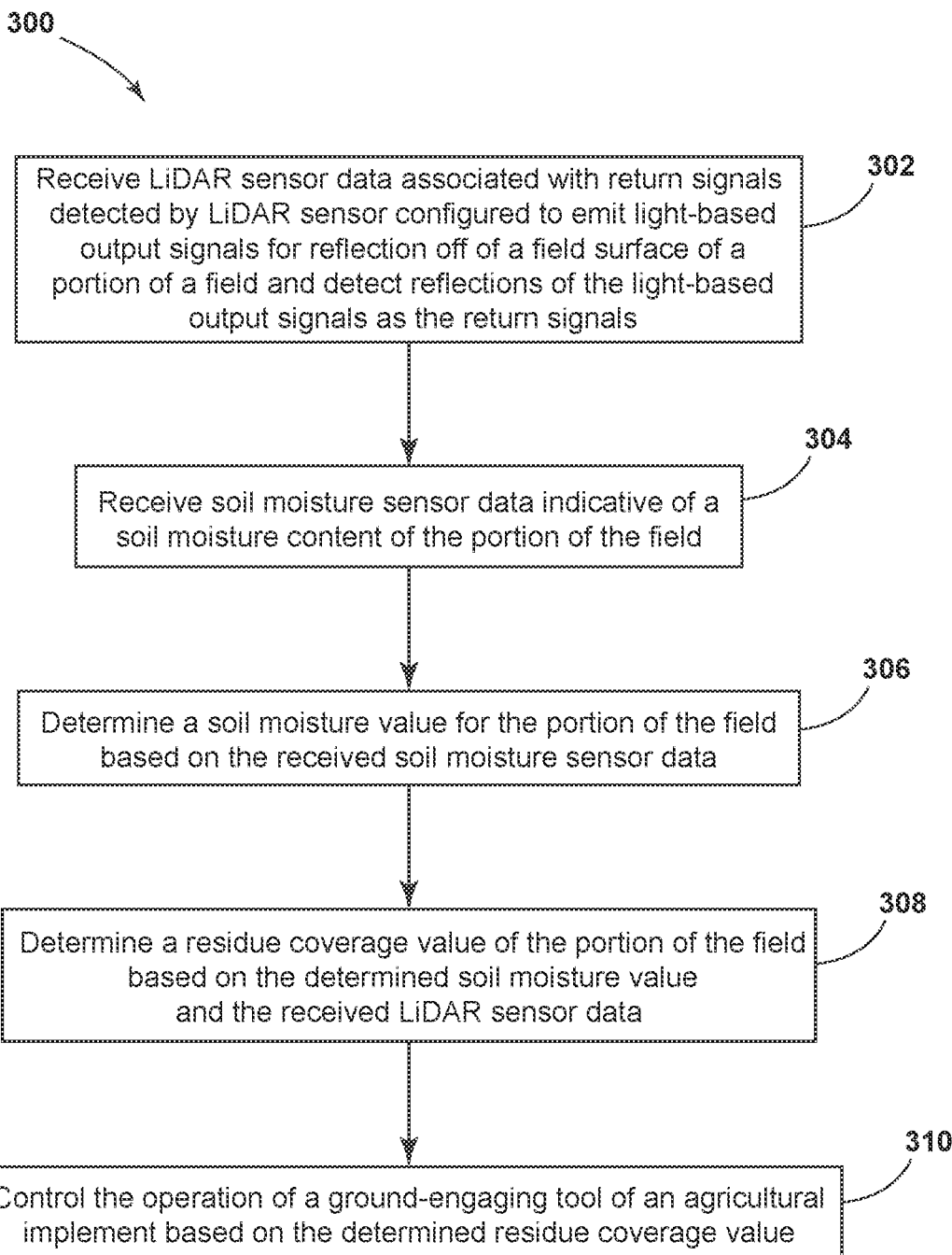

300

Receive LiDAR sensor data associated with return signals
detected by LiDAR sensor configured to emit light-based
output signals for reflection off of a field surface of a
portion of a field and detect reflections of the light-based
output signals as the return signals                              302

Receive soil moisture sensor data indicative of a
soil moisture content of the portion of the field                304

Determine a soil moisture value for the portion of the field
based on the received soil moisture sensor data                  306

Determine a residue coverage value of the portion of the field
based on the determined soil moisture value
and the received LiDAR sensor data                               308

Control the operation of a ground-engaging tool of an agricultural
implement based on the determined residue coverage value         310

FIG. 6

SYSTEM AND METHOD FOR DETERMINING RESIDUE COVERAGE OF A FIELD

FIELD OF THE INVENTION

The present disclosure generally relates to the acquisition and analysis of surface condition data associated with an agricultural field and, more particularly, to systems and methods for determining residue coverage of an agricultural field.

BACKGROUND OF THE INVENTION

Residue generally refers to the vegetation (e.g., straw, chaff, husks, cobs, etc.) remaining on the soil surface following the performance of a given agricultural operation, such as a harvesting operation or a tillage operation. For various reasons, it is important to maintain a given amount of residue within a field following an agricultural operation. Specifically, residue remaining within the field can help maintain the content of organic matter within the soil and protect the soil from wind and water erosion. However, in some cases, leaving an excessive amount of crop residue within a field can have a negative effect on the productivity potential of the soil, such as by slowing down the warming of the soil at planting time and/or by slowing down seed germination.

As such, the ability to monitor and/or adjust the amount of residue remaining within a field can be important to maintaining a healthy, productive field, particularly when it comes to performing tillage operations. In this respect, systems and methods have been developed that estimate residue coverage of an agricultural field. While such systems and methods generally work well, further improvements are needed.

Accordingly, an improved system and method for determining residue coverage of a field would be welcomed in the technology.

SUMMARY OF THE INVENTION

Aspects and advantages of the technology will be set forth in part in the following description, or may be obvious from the description, or may be learned through practice of the technology.

In one aspect, the present subject matter is directed to an agricultural implement including a frame and a ground-engaging tool supported on the frame, with the ground-engaging tool configured to engage soil within a field as the agricultural implement travels across the field. The agricultural implement also includes a LiDAR sensor configured to emit light-based output signals for reflection off of a field surface of a portion of the field and detect reflections of the light-based output signals as return signals. Furthermore, the agricultural implement includes a soil moisture sensor configured to generate soil moisture sensor data indicative of a soil moisture content of the portion of the field. Additionally, the agricultural implement includes a computing system communicatively coupled to the LiDAR sensor and the soil moisture sensor. In this respect, the computing system is configured to receive LiDAR sensor data associated with the return signals detected by the LiDAR sensor. Moreover, the computing system is configured to determine a soil moisture value for the portion of the field based on the soil moisture sensor data. In addition, the computing system is configured to determine a residue coverage value for the portion of the field based on the determined soil moisture value and the received LiDAR sensor data and control an operation of the ground-engaging tool based on the determined residue coverage value.

In another aspect, the present subject matter is directed to a system for determining residue coverage of a field. The system includes a LiDAR sensor configured to emit light-based output signals for reflection off of a field surface of a portion of the field and detect reflections of the light-based output signals as return signals. Furthermore, the system includes a soil moisture sensor configured to generate soil moisture sensor data indicative of a soil moisture content of the portion of the field. Additionally, the system includes a computing system communicatively coupled to the LiDAR sensor and the soil moisture sensor. As such, the computing system is configured to receive LiDAR sensor data associated with the return signals detected by the LiDAR sensor. Moreover, the computing system is configured to determine a soil moisture value for the portion of the field based on the soil moisture sensor data. In addition, the computing system is configured to determine a residue coverage value of the portion of the field based on the determined soil moisture value and the LiDAR sensor data.

In a further aspect, the present subject matter is directed to a method for determining residue coverage of a field. The method includes receiving, with a computing system, LiDAR sensor data associated with return signals detected by a LiDAR sensor configured to emit light-based output signals for reflection off of a field surface of a portion of the field and detect reflections of the light-based output signals as the return signals. Furthermore, the method includes receiving, with the computing system, soil moisture sensor data indicative of a soil moisture content of the portion of the field. Additionally, the method includes determining, with the computing system, a soil moisture value for the portion of the field based on the received soil moisture sensor data. Moreover, the method includes determining, with the computing system, a residue coverage value of the portion of the field based on the determined soil moisture value and the received LiDAR sensor data. In addition, the method includes controlling, with the computing system, an operation of a ground-engaging tool of an agricultural implement based on the determined residue coverage value.

These and other features, aspects and advantages of the present technology will become better understood with reference to the following description and appended claims. The accompanying drawings, which are incorporated in and constitute a part of this specification, illustrate embodiments of the technology and, together with the description, serve to explain the principles of the technology.

BRIEF DESCRIPTION OF THE DRAWINGS

A full and enabling disclosure of the present technology, including the best mode thereof, directed to one of ordinary skill in the art, is set forth in the specification, which makes reference to the appended figures, in which:

FIG. 6 illustrates a flow diagram of one embodiment of a method for determining residue coverage of a field in accordance with aspects of the present subject matter.

Figure 1:
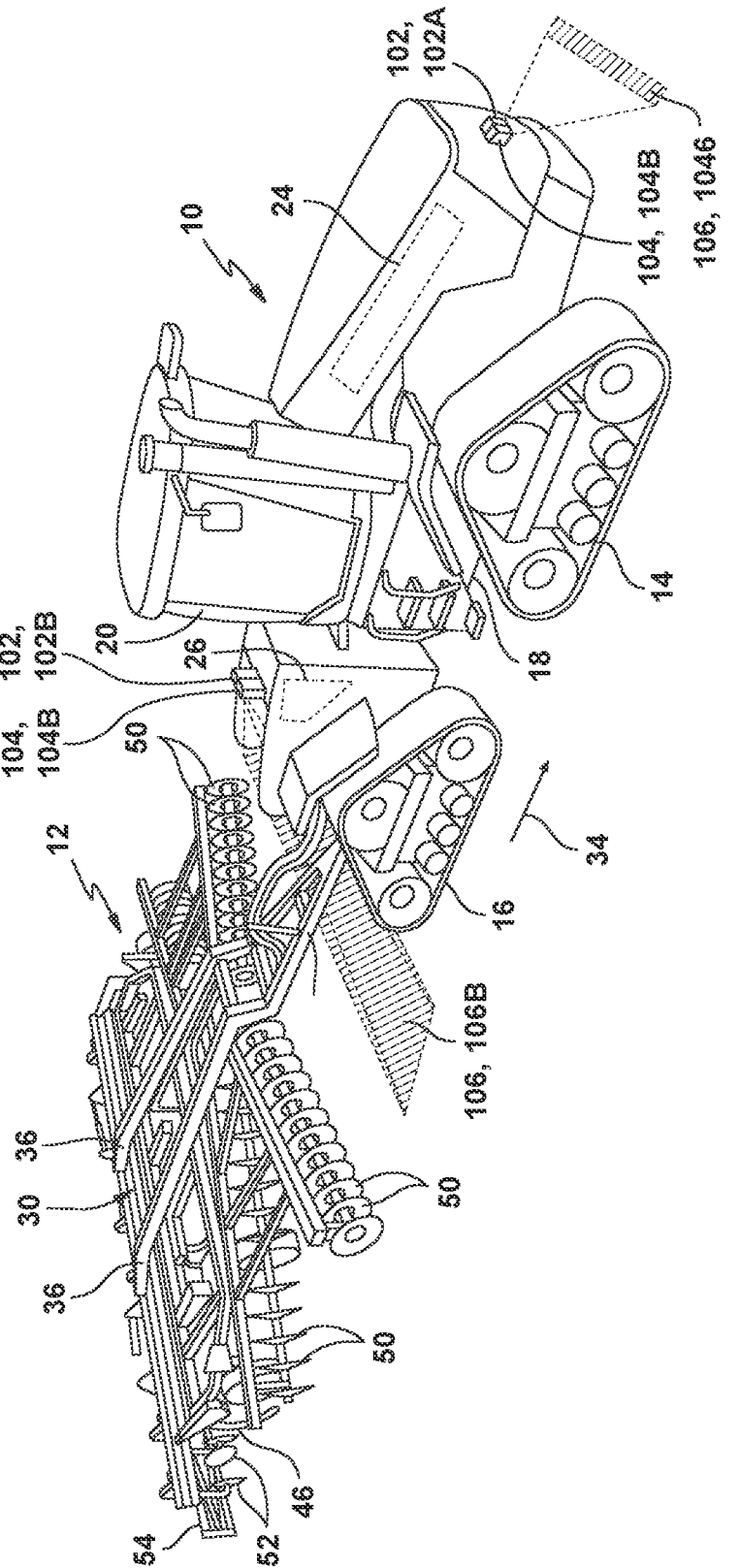
FIG. 1 illustrates a perspective view of one embodiment of an agricultural implement coupled to a work vehicle in accordance with aspects of the present subject matter.

Repeat use of reference characters in the present specification and drawings is intended to represent the same or analogous features or elements of the present technology.

DETAILED DESCRIPTION OF THE DRAWINGS

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield still a further embodiment. Thus, it is intended that the present invention covers such modifications and variations as come within the scope of the appended claims and their equivalents.

In general, the present subject matter is directed to a system and a method for determining residue coverage of a field. As will be described below, the disclosed system and method may be implemented on an agricultural implement (e.g., a tillage implement) and/or an associated work vehicle (e.g., an agricultural tractor). As such, in several embodiments, the disclosed system includes a LiDAR sensor and a soil moisture sensor mounted on or otherwise supported on the agricultural implement or work vehicle. The LiDAR sensor, in turn, is configured to emit light-based output signals for reflection off of the surface of a portion of the field and detect reflections of the light-based output signals as return signals. Conversely, the soil moisture sensor is configured to generate soil moisture sensor data indicative of a soil moisture content of the portion of the field.

Furthermore, a computing system of the disclosed system is configured to determine the residue coverage of the portion of the field based on the LiDAR sensor data and the soil moisture sensor data. More specifically, in several embodiments, the computing system is configured to determine a soil moisture value for the portion of the field based on the soil moisture sensor data. Additionally, in some embodiments, the computing system is configured to determine a reflectivity value of the output signals off of the soil within the portion of the field based on the determined soil moisture content value. Moreover, the computing system may be configured to determine the residue coverage value of the portion of the field based on the determined reflectivity value and the received LiDAR sensor data. For example, in one embodiment, the computing system may identify sections of the portion of the field exhibiting the determined reflectivity value and sections of the portion of the field not exhibiting the determined reflectivity value. Thereafter, the computing system may determine the residue coverage value of the portion of the field based on the identified sections of the portion of the field not exhibiting the determined reflectivity value (e.g., the amount of area of the portion the field occupied by the sections not having the determined reflectivity value). In addition, the computing system may be configured to control the operation of one or more ground-engaging tools of the agricultural implement based on the determined residue coverage value.

The disclosed system and method improve the operation of the agricultural implement and/or work vehicle on which such system and method is implemented. More specifically, LiDAR sensor data can be used to determine residue coverage based on the differences in reflectivity of the light-based output signals off of the soil and residue within the field. However, moisture content affects the reflectivity of the light-based output signals off of the soil and the residue within the field. Moreover, moisture content can vary widely in both the soil and the residue throughout a given field. As described above, the disclosed system uses soil moisture content to determine a reflectivity value for the soil and then determines the residue coverage based on the sections of the portion of the field being analyzed that do not have the determined reflectivity value. Thus, the disclosed system and method allow for an accurate determination of residue coverage without requiring significant computing resources as soil moisture content varies throughout the field.

Figure 2:
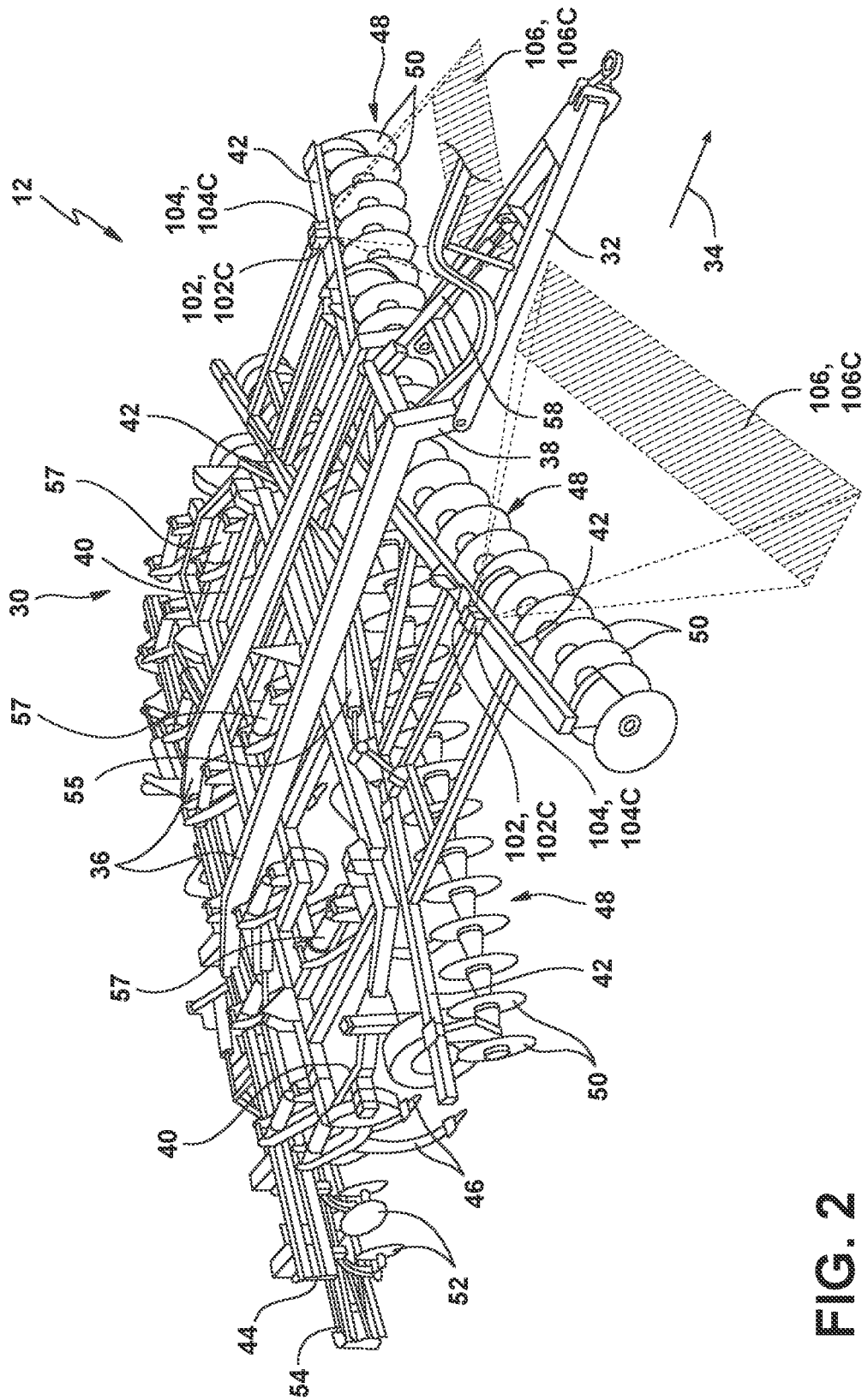
FIG. 2 illustrates another perspective view of the agricultural implement shown in FIG. 1, particularly illustrating various ground-engaging tools of the implement.

Referring now to drawings, FIGS. 1 and 2 illustrate perspective views of one embodiment of a work vehicle 10 and an associated agricultural implement 12. Specifically, FIG. 1 illustrates a perspective view of the work vehicle 10 towing the agricultural implement 12 (e.g., across a field). Additionally, FIG. 2 illustrates a perspective view of the agricultural implement 12 shown in FIG. 1.

As shown, in the illustrated embodiment, the work vehicle 10 is configured as an agricultural tractor and the agricultural implement 12 is configured as a tillage implement (e.g., a disk ripper). However, in other embodiments, the work vehicle 10 may be configured as any other suitable vehicle configured to tow an agricultural implement. Similarly, the agricultural implement 12 may be configured as any other suitable type of implement, such as another type of tillage implement, a seed-planting implement, a fertilizing implement, and/or the like.

As particularly shown in FIG. 1, the work vehicle 10 includes a pair of front track assemblies 14, a pair of rear track assemblies 16, and a frame or chassis 18 coupled to and supported by the track assemblies 14, 16. An operator's cab 20 may be supported by a portion of the chassis 18 and may house various input devices for permitting an operator to control the operation of one or more components of the work vehicle 10 and/or one or more components of the agricultural implement 12. Additionally, the work vehicle 10 may include an engine 24 and a transmission 26 mounted on the chassis 18. The transmission 26 may be operably coupled to the engine 24 and may provide variably adjusted gear ratios for transferring engine power to the track assemblies 14, 16 via a drive axle assembly (not shown) (or via axles if multiple drive axles are employed). Furthermore, the work vehicle 10 can have any other suitable traction device(s), such as wheels or tires, and/or any other suitable transmission/engine configuration.

Moreover, as shown in FIGS. 1 and 2, the agricultural implement 12 includes a carriage frame assembly 30 configured to be towed by the work vehicle 10 via a pull hitch or tow bar 32 in a direction of travel of the vehicle (e.g., as indicated by arrow 34). In this respect, the carriage frame assembly 30 may be configured to support a plurality of ground-engaging tools, such as a plurality of shanks, disk blades, leveling blades, basket assemblies, and/or the like. As such, the various ground-engaging tools may be configured to perform an agricultural operation (e.g., a tillage operation) on the field across which the agricultural implement 12 is being towed.

As particularly shown in FIG. 2, the carriage frame assembly 30 may include aft extending carrier frame members 36 coupled to the tow bar 32. In addition, reinforcing gusset plates 38 may be used to strengthen the connection between the tow bar 32 and the carrier frame members 36. In several embodiments, the carriage frame assembly 30 may support a central frame 40, a forward frame 42 positioned forward of the central frame 40 relative to the direction of travel 34 of the work vehicle 10, and an aft frame 44 positioned aft of the central frame 40 relative to the direction of travel 34 of the work vehicle 10. As shown in FIG. 2, in one embodiment, the central frame 40 may correspond to a shank frame configured to support a plurality of ground-engaging shanks 46. In such an embodiment, the shanks 46 may be configured to till the soil as the agricultural implement 12 is towed across the field. However, in other embodiments, the central frame 40 may be configured to support any other suitable ground-engaging tools.

Additionally, as shown in FIG. 2, in one embodiment, the forward frame 42 may correspond to a disk frame configured to support various gangs or sets 48 of disk blades 50. In such an embodiment, each disk blade 50 may, for example, include both a concave side (not shown) and a convex side (not shown). In addition, the various gangs 48 of disk blades 50 may be oriented at an angle relative to the travel direction 34 of the work vehicle 10 to promote more effective tilling of the soil. However, in other embodiments, the forward frame 42 may be configured to support any other suitable ground-engaging tools.

Moreover, like the central and forward frames 40, 42, the aft frame 44 may also be configured to support a plurality of ground-engaging tools. For instance, in the illustrated embodiment, the aft frame is configured to support a plurality of leveling blades 52 and rolling (or crumbler) basket assemblies 54. However, in other embodiments, any other suitable ground-engaging tools may be coupled to and supported by the aft frame 44, such as a plurality of closing disks.

Furthermore, the agricultural implement 12 may also include any number of suitable ground-engaging tool actuators (e.g., hydraulic cylinders) for adjusting the relative positioning of, the penetration depth of, and/or the force being applied to the various ground-engaging tools 46, 50, 52, 54. For instance, in the illustrated embodiment, the implement 12 may include one or more actuators 57 coupled to the central frame 40 for raising and/or lowering the central frame 40 relative to the ground, thereby allowing the penetration depth of and/or the force being applied to the shanks 46 to be adjusted. Similarly, the implement 12 may include one or more actuators 55 coupled to the forward frame 42 to adjust the penetration depth of and/or the force being applied to the disk blades 50.

Additionally, as shown in FIGS. 1 and 2, the work vehicle 10 and/or the agricultural implement 12 may include one or more LiDAR sensors 102 coupled thereto and/or supported thereon. In general, the LiDAR sensor(s) 102 is configured to emit light-based output signals for reflection off of the field surface of a portion of the field across which the vehicle/implement 10/12 are traveling. Moreover, the LiDAR sensor(s) 102 is configured to detect the reflections of the light-based output signals as return signals. Specifically, in several embodiments, the LiDAR sensor(s) 102 may be provided in operative association with the work vehicle 10 such that the LiDAR sensor(s) 102 has a field(s) of view 106 directed towards a portion(s) of the field disposed in front of or behind the work vehicle 10. Moreover, or alternatively, the LiDAR sensor(s) 102 may be provided in operative association with the agricultural implement 12 such that the LiDAR sensor(s) 102 has a field(s) of view 106 directed towards a portion(s) of the field disposed in front of the agricultural implement 12 as the agricultural implement 12 is being towed across the field. As such, the LiDAR sensor(s) 102 may generate LiDAR data associated with the detected return signals (e.g., the light-based output signals reflected off of the portion(s) of the field within the field(s) of view 106) as the vehicle/implement 10/12 travels across the field. As will be described below, LiDAR data associated with the detected return signals is used with soil moisture data to determine the residue coverage of the portion of the field.

Furthermore, as shown in FIGS. 1 and 2, the work vehicle 10 and/or the agricultural implement 12 may include one or more soil moisture sensors 104 coupled thereto and/or supported thereon. In general, the soil moisture sensor(s) 104 is configured to generate data indicative of the soil moisture content of the field across which the vehicle/implement 10/12 are traveling. Specifically, in several embodiments, the soil moisture sensor(s) 104 may be provided in operative association with the work vehicle 10 such that the soil moisture sensor(s) 104 has a field(s) of view 106 directed towards a portion(s) of the field disposed in front of or behind the work vehicle 10. Additionally, or alternatively, the soil moisture sensor(s) 104 may be provided in operative association with the agricultural implement 12 such that the soil moisture sensor(s) 104 has a field(s) of view 106 directed towards a portion(s) of the field disposed in front of the agricultural implement 12 as the agricultural implement 12 is being towed across the field. As such, the soil moisture sensor(s) 104 may generate soil moisture data associated with one or more portion(s) of the field in front of the agricultural implement 12 (and, more specifically, the disk blades 50 of the agricultural implement 12) as the vehicle/implement 10/12 travels across the field. As will be described below, soil moisture sensor data is used with the LiDAR sensor data to determine the residue coverage of the portion of the field.

In general, the soil moisture sensor(s) 104 may correspond to any suitable device(s) configured to generate data indicative of the soil moisture content of the field. For example, in several embodiments, the soil moisture sensor(s) 104 may be configured as a microwave-based sensor(s) (e.g., a ground-penetrating radar (GPR) sensor) configured to emit one or more microwave-based output signals directed toward the soil within the field(s) of view 106. A portion of the microwave-based output signal(s) is, in turn, backscattered or otherwise reflected by the soil as an echo signal(s). In this respect, the soil moisture sensor(s) 104 receives the echo signal(s), which is indicative of a backscattering of the output signal(s) by the soil. Thus, the received echo signal(s) is indicative of the soil moisture content of the portion of the field. However, in alternative embodiments, the soil moisture sensor(s) 104 may be configured as any other suitable device(s) for sensing or detecting the soil moisture content of the field, such as an optical sensor(s), an electromagnetic inductance (EMI) sensor(s), etc.

The work vehicle 10 and/or the agricultural implement 12 may include any number of LiDAR sensor(s) 102 and/or soil moisture sensor(s) 104 provided at any suitable location(s) on the work vehicle 10 and/or the agricultural implement 12.

In this respect, FIGS. 1 and 2 illustrate example locations for mounting the LiDAR sensor(s) 102 and the soil moisture sensor(s) 104. For example, as shown in FIG. 1, in one embodiment, one or more LiDAR sensors 102A and one or more soil moisture sensors 104A are coupled to the front of the work vehicle 10 such that the LiDAR sensor(s) 102A and the soil moisture sensor(s) 104A have a fields of view 106A directed at an area or portion of the field disposed in front of the work vehicle 10 and, thus, in front of the agricultural implement 12. In addition to the LiDAR sensor(s) 102A and the soil moisture sensor(s) 104A (or as an alternative thereto), one or more LiDAR sensors 102B and one or more soil moisture sensors 104B may be coupled to the rear of the work vehicle 10 such that the LiDAR sensor(s) 102B and the soil moisture sensor(s) 104B have a fields of view 106B directed at an area or portion of the field disposed aft of the work vehicle 10 and forward of the agricultural implement 12. In addition to the LiDAR sensors 102A, 102B and the soil moisture sensors 104A, 104B (or as an alternative thereto), one or more LiDAR sensors 102C and one or more soil moisture sensors 104C may also be coupled to the front of the agricultural implement 12 such that the LiDAR sensor(s) 102A and the soil moisture sensor(s) 104A have a fields of view 106C directed at an area or portion of the field disposed in front of the agricultural implement 12. However, in alternative embodiments, the LiDAR sensor(s) 102 and/or soil moisture sensor(s) 104 may be installed at any other suitable location(s). Moreover, although FIGS. 1 and 2 show the LiDAR sensors 102 and the soil moisture sensors 104 being at the same general locations and having the same general fields of view 106, the LiDAR sensor(s) 102 and soil moisture sensor(s) 104 may be positioned at different locations and/or have different fields of view.

Figure 3:
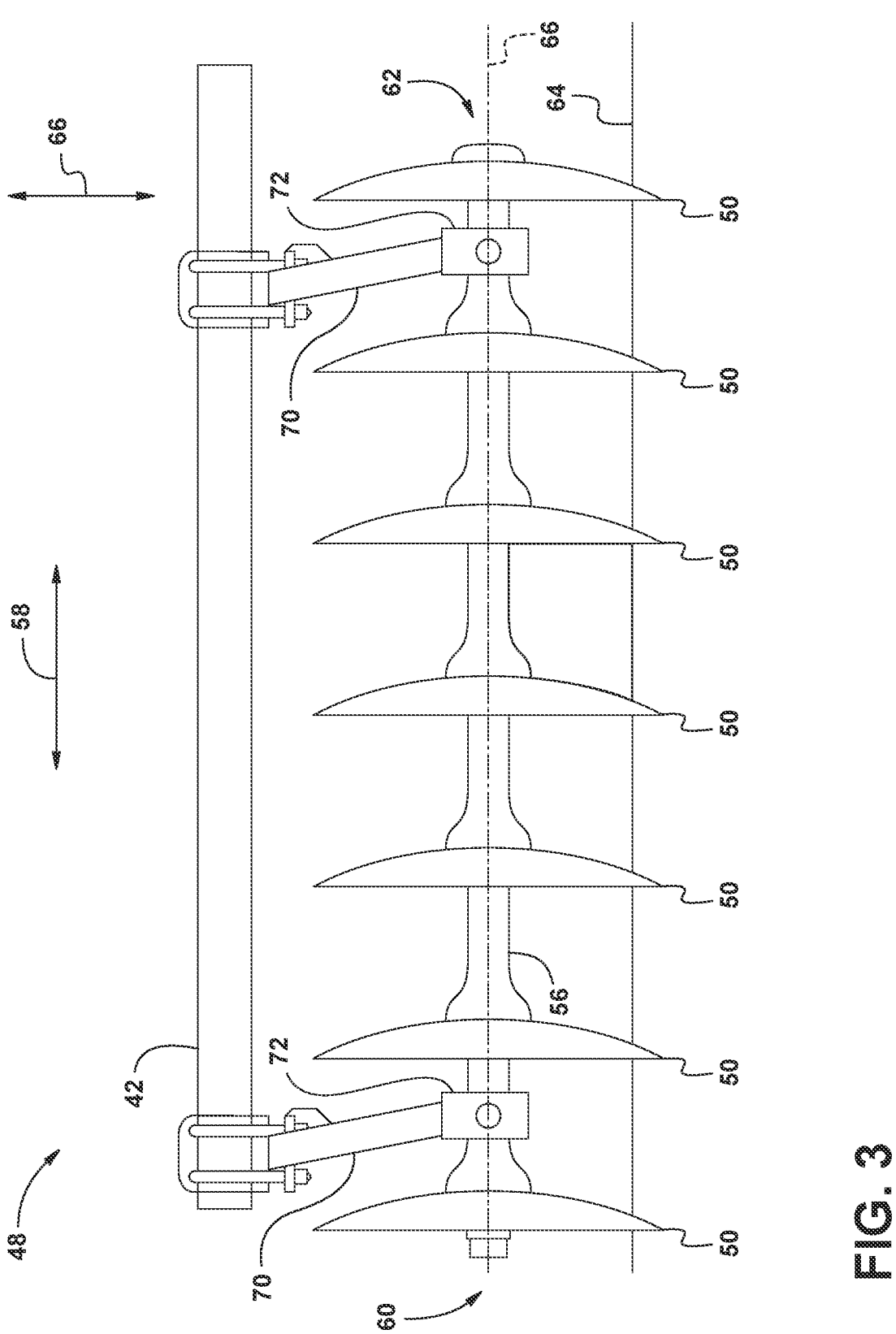
FIG. 3 illustrates a front view of one embodiment of a disk gang of an agricultural implement in accordance with aspects of the present subject matter.

Referring now to FIG. 3, a front view of one embodiment of a disk gang 48 of the agricultural implement 12 is illustrated in accordance with aspects of the present subject matter. Specifically, in several embodiments, the disk gang 48 may include a disk gang shaft 56 that extends along an axial direction or length of the disk gang 48 (e.g., as indicated by arrow 58 in FIG. 3) between a first end 60 and a second end 62. As shown, the disks 50 are coupled to the disk gang shaft 56 and spaced apart from each other along the axial direction 58. As the agricultural implement 12 is moved across a field, the disks 50 may be configured to penetrate the soil surface (e.g., as indicated by line 64 in FIG. 3) of the field and rotate about an axis of rotation (e.g., as indicated by dashed line 66 in FIG. 3) relative to the soil within the field.

In general, the disk gang 48 is supported relative to the forward frame 42 of the agricultural implement 12. Specifically, in several embodiments, a pair of hangers 70 (e.g., C-hangers) support the disk gang 48 at a position below the forward frame 42. For example, in one embodiment, one end of each hanger 70 may be coupled to the forward frame 42, while the opposing end of each hanger 70 is coupled to a bearing block 72. The bearing blocks 72, in turn, are rotatably coupled to the disk gang shaft 56. However, in alternative embodiments, the disk gang 48 may have any other suitable configuration.

The configuration of the work vehicle 10 and the agricultural implement 12 described above and shown in FIGS. 1-3 is provided only to place the present subject matter in an exemplary field of use. Thus, the present subject matter may be readily adaptable to any manner of vehicle and/or implement configuration.

Figure 4:
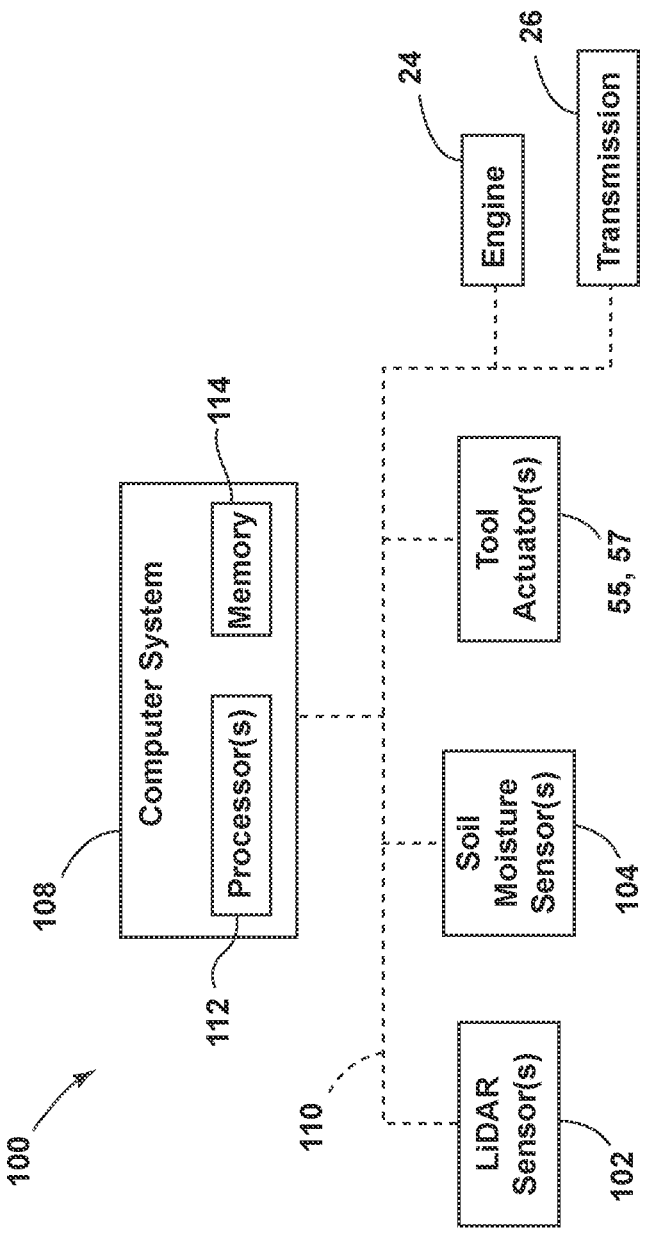
FIG. 4 illustrates a schematic view of one embodiment of a system for determining residue coverage of a field in accordance with aspects of the present subject matter.

Referring now to FIG. 4, a schematic view of one embodiment of a system 100 for determining residue coverage of a field is illustrated in accordance with aspects of the present subject matter. In general, the system 100 will be described herein with reference to the work vehicle 10 and the agricultural implement 12 described above with reference to FIGS. 1-3. However, it should be appreciated by those of ordinary skill in the art that the disclosed system 100 may generally be utilized with work vehicles having any other suitable vehicle configuration and/or agricultural implements having any other suitable implement configuration.

As shown in FIG. 4, the system 100 includes one or more components of the work vehicle 10 and/or the agricultural implement 12. For example, in the illustrated embodiment, the system 100 includes the LiDAR sensor(s) 102; the soil moisture sensor(s) 104; the ground-engaging tool actuator(s) 55, 57; the engine 24; and the transmission 26. However, in alternative embodiments, the system 100 may include any other suitable components of the work vehicle 10 and/or the agricultural implement 12.

Moreover, the system 100 includes a computing system 108 communicatively coupled to one or more components of the work vehicle 10, the agricultural implement 12, and/or the system 100 to allow the operation of such components to be electronically or automatically controlled by the computing system 108. For instance, the computing system 108 may be communicatively coupled to the LiDAR sensor(s) 102 and the soil moisture sensor(s) 104 via a communicative link 110. As such, the computing system 108 may be configured to receive data from the LiDAR sensor(s) 102 and the soil moisture sensor(s) 104 that are used to determine the residue coverage of the field across which the vehicle/implement 10/12 are traveling. Furthermore, the computing system 108 may be communicatively coupled to the engine 24, the transmission 26, and/or the ground-engaging tool actuator(s) 55, 57 via the communicative link 110. In this respect, the computing system 108 may be configured to control the operation of the components 24, 26, 55, 57 to adjust the operation of such components 24, 26, 55, 57 based on the determined residue coverage. In addition, the computing system 108 may be communicatively coupled to any other suitable components of the work vehicle 10, the agricultural implement 12, and/or the system 100.

In general, the computing system 108 may comprise one or more processor-based devices, such as a given controller or computing device or any suitable combination of controllers or computing devices. Thus, in several embodiments, the computing system 108 may include one or more processor(s) 112 and associated memory device(s) 114 configured to perform a variety of computer-implemented functions. As used herein, the term "processor" refers not only to integrated circuits referred to in the art as being included in a computer, but also refers to a controller, a microcontroller, a microcomputer, a programmable logic circuit (PLC), an application specific integrated circuit, and other programmable circuits. Additionally, the memory device(s) 114 of the computing system 108 may generally comprise memory element(s) including, but not limited to, a computer readable medium (e.g., random access memory RAM)), a computer readable non-volatile medium (e.g., a flash memory), a floppy disk, a compact disk-read only memory (CD-ROM), a magneto-optical disk (MOD), a digital versatile disk (DVD) and/or other suitable memory elements. Such memory device(s) 114 may generally be configured to store suitable computer-readable instructions that, when implemented by the processor(s) 112, configure the computing system 108 to perform various computer-implemented functions, such as one or more aspects of the methods and algorithms that will be described herein. In addition, the computing system 108 may also include various other suitable components, such as a communications circuit or module, one or more input/output channels, a data/control bus and/or the like.

The various functions of the computing system 108 may be performed by a single processor-based device or may be distributed across any number of processor-based devices, in which instance such devices may be considered to form part of the computing system 108. For instance, the functions of the computing system 108 may be distributed across multiple application-specific controllers or computing devices, such as a navigation controller, an engine controller, a transmission controller, an implement controller, and/or the like.

Figure 5:
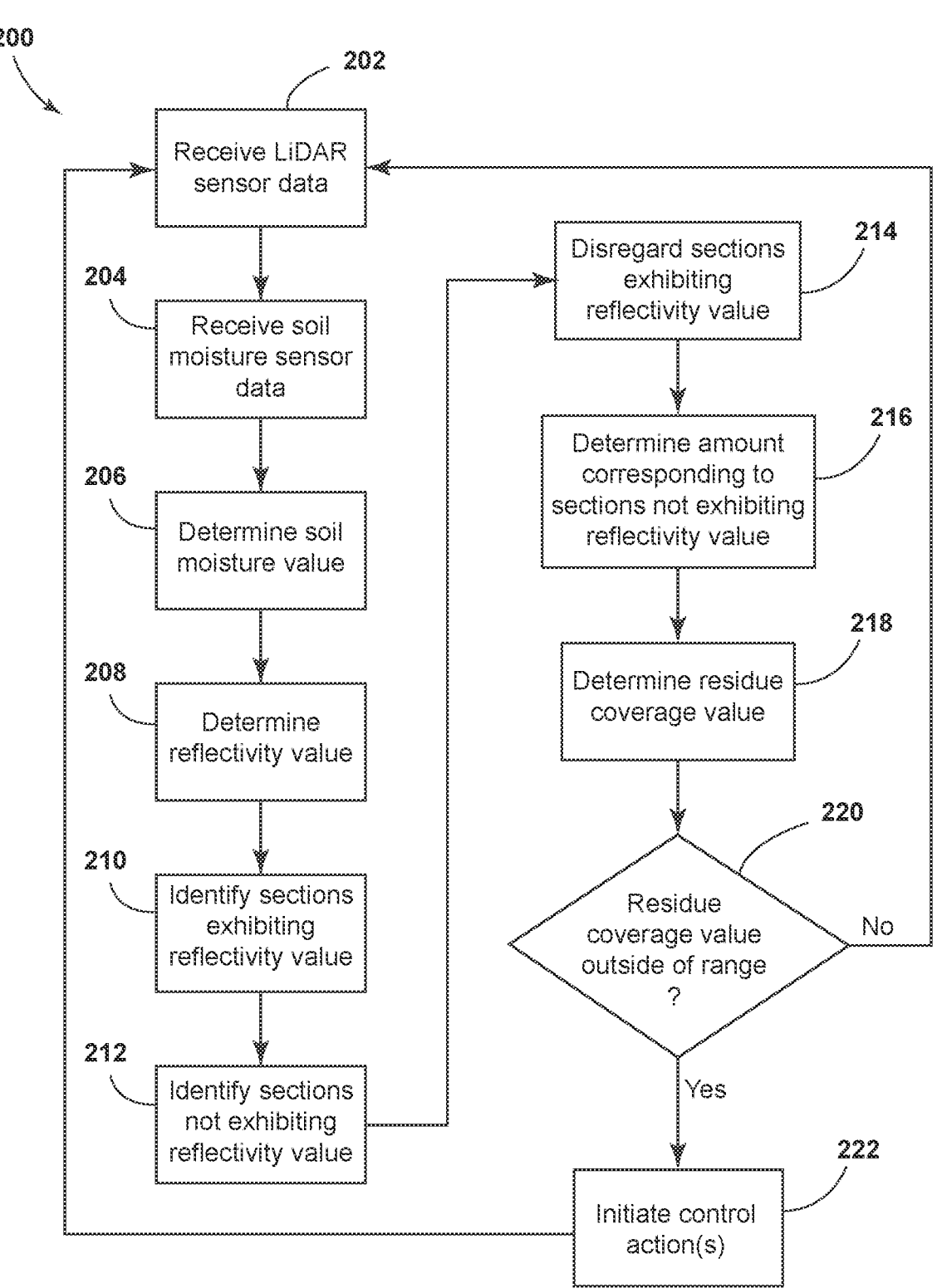
FIG. 5 illustrates a flow diagram providing one embodiment of control logic for determining residue coverage of a field in accordance with aspects of the present subject matter.

Referring now to FIG. 5, a flow diagram of one embodiment of example control logic 200 that may be executed by the computing system 108 (or any other suitable computing system) for determining residue coverage of a field is illustrated in accordance with aspects of the present subject matter. Specifically, the control logic 200 shown in FIG. 5 is representative of steps of one embodiment of an algorithm that can be executed to determine the residue coverage of a field without requiring substantial computing resources and/or processing time. However, in other embodiments, the control logic 200 may be used in association with any other suitable system, application, and/or the like for determining the residue coverage of a field.

As shown, at (202), the control logic 200 includes receiving LiDAR sensor data associated with return signals detected by a LiDAR sensor. Specifically, as mentioned above, in several embodiments, the computing system 108 may be communicatively coupled to the LiDAR sensor(s) 102 via the communicative link 110. The LiDAR sensor(s) 102, in turn, is configured to emit light-based output signals for reflection off of the surface of a portion of the field within the field(s) of view 106 and detect reflections of the light-based output signals as the return signals. In this respect, as the vehicle/implement 10/12 travels across the field to perform an operation (e.g., a tillage operation) thereon, the computing system 108 may receive LiDAR sensor data from the LiDAR sensor(s) 102. Such LiDAR sensor data may, in turn, be associated with or indicative of the return signals detected by a LiDAR sensor(s) 102.

Furthermore, at (204), the control logic 200 includes receiving soil moisture sensor data indicative of the soil moisture content of the portion of the field. Specifically, as mentioned above, in several embodiments, the computing system 108 may be communicatively coupled to the soil moisture sensor(s) 104 via the communicative link 110. In this respect, as the vehicle/implement 10/12 travels across the field to perform the operation thereon, the computing system 108 may receive soil moisture sensor data from the soil moisture sensor(s) 104. Such soil moisture sensor data may, in turn, be indicative of the soil moisture content of the portion of the field.

Additionally, at (206), the control logic 200 includes determining a soil moisture value for the portion of the field based on the received soil moisture sensor data. Specifically, in several embodiments, the computing system 108 is configured to analyze the soil moisture sensor data received at (204) to determine a soil moisture value for the portion of the field. For example, the computing system 108 may include any suitable look-up table(s), mathematical equation(s), and/or algorithm(s) stored within its memory device(s) 114 that correlate the received soil moisture sensor data to the corresponding soil moisture content value(s). As will be described below, the computing system 108 is configured to determine a residue coverage value for the portion of the field based on the soil moisture value determined at (206) and the LiDAR sensor data received at (202).

Moreover, at (208), the control logic 200 includes determining a reflectivity value of the output signals off of the soil within the field based on the determined soil moisture content value. More specifically, as mentioned above, the moisture content affects the reflectivity of the light-based output signals emitted by the LiDAR sensor(s) 102 off of the soil within the field. As such, in several embodiments, the computing system 108 is configured to determine a reflectivity value of the output signals off of the soil within the field based on the soil moisture content value determined at (206). For example, the computing system 108 may include any suitable look-up table(s), mathematical equation(s), and/or algorithm(s) stored within its memory device(s) 114 that correlates soil moisture content value(s) to the corresponding reflectivity value(s). As will be described below, the computing system 108 is configured to determine the residue coverage value of the portion of the field based on the reflectivity value determined at (208) and the LiDAR sensor data received at (210).

In addition, at (210), the control logic 200 includes identifying sections of the portion of the field exhibiting the determined reflectivity value. Specifically, in several embodiments, the computing system 108 is configured to analyze the LiDAR sensor data received at (202) to identify sections of the portion of the field exhibiting or otherwise having the reflectivity value determined at (208). Such sections of the portion of the field exhibiting the determined reflectivity value correspond to areas of the portion of the field that are not covered in residue.

As shown in FIG. 5, at (212), the control logic 200 includes identifying sections of the portion of the field not exhibiting the determined reflectivity value. Specifically, in several embodiments, the computing system 108 is configured to analyze the LiDAR sensor data received at (202) to identify sections of the portion of the field not exhibiting or otherwise having the reflectivity value determined at (208). Such sections of the portion of the field not exhibiting the determined reflectivity value correspond to areas of the portion of the field that are covered in residue.

Furthermore, at (214), the control logic 200 includes disregarding the identified sections of the portion of the field exhibiting the determined reflectivity value. Specifically, in several embodiments, the computing system 108 is configured to disregard the sections of the portion of the field identified at (210) as exhibiting the reflectivity value determined at (208). That is, at (214), the computing system 108 disregards the sections of the portion of the field that are not covered in residue, thereby leaving only the portions of the field covered in residue (i.e., the sections of the portion of the field not exhibiting the determined reflectivity value).

Additionally, at (216), the control logic 200 includes determining the amount of the portion of the field corresponding to the identified sections of the portion of the field not exhibiting the determined reflectivity value. Specifically, in several embodiments, the computing system 108 is configured to determine the amount or proportion of the portion of the field corresponding to the sections of the portion of the field identified at (212) as not exhibiting the reflectivity value determined at (208). That is, at (216), the computing system 108 determines the amount or proportion of the portion of the field covered in residue.

Moreover, at (218), the control logic 200 includes determining the residue coverage value of the portion of the field based on the determined amount. Specifically, in several embodiments, the computing system 108 is configured to determine the residue coverage value of the portion of the field based on the amount determined at (216). For example, in one embodiment, the residue coverage value may be percent residue coverage. In such instances, the computing system 108 may convert the amount determined at (216) into a percentage of the portion of the field that is covered by residue. However, in alternative embodiments, the residue coverage value may be any other suitable value or parameter indicative of the residue coverage of the portion of the field. As will be described below, the computing system 108 may be configured to control the operation of one or more of the ground-engaging tools of the agricultural implement 12, such as the disk blades 50 and/or the shanks 46, based on the residue coverage value determined at (218).

In addition, at (220), the control logic 200 includes comparing the determined residue coverage value to a range. Specifically, in several embodiments, the computing system 108 is configured to compare the residue coverage value determined at (218) to a range, such as a predetermined range. When the determined residue coverage value is within the range, the portion of the field has the selected or desired residue coverage. In such instances, the control logic 200 returns to (202). Conversely, when determined residue coverage value is outside of the range, the field does not have the selected or desired residue coverage. In such instances, the control logic 200 proceeds to (222).

Furthermore, at (222), the control logic 200 includes initiating one or more control actions when the determined residue coverage value falls outside of the range. Specifically, in several embodiments, when it is determined at (220) that the residue coverage value determined at (218) is outside of the range, the computing system 108 is configured to initiate one or more control actions. For example, in one embodiment, the control action(s) may include providing a notification to an operator of vehicle/implement 10/12 indicating that the determined residue coverage value falls outside of the range.

Additionally, or alternatively, the control action(s) may include actively adjusting one or more components of the work vehicle 10 and/or the agricultural implement 12. For example, in some embodiments, the computing system 108 may initiate an adjustment to the penetration depth(s) of the ground-engaging tool(s) of the implement 12. For example, the computing system 108 may transmit suitable control signals to the actuator(s) 55 and/or the actuator(s) 57 instructing the actuator(s) 55 and/or the actuator(s) 57 to adjust the penetration depths of the disk blades 50 and/or the shanks 46. Similarly, the computing system 108 may initiate an adjustment to the ground speed of the vehicle/implement 10/12. For example, the computing system 108 may transmit suitable control signals to the engine 24 and/or the transmission 26 instructing the engine 24 and/or the transmission 26 to adjust (e.g., reduce) the ground speed of the vehicle/implement 10/12. However, in alternative embodiments, any other suitable control action(s) may be initiated at (222) in addition to or in lieu of the control actions described above. Upon completion of (222), the control logic 200 returns to (202).

Referring now to FIG. 6, a flow diagram of one embodiment of a method 300 for determining residue coverage of a field is illustrated in accordance with aspects of the present subject matter. In general, the method 300 will be described herein with reference to the work vehicle 10, the agricultural implement 12, and the system 100 described above with reference to FIGS. 1-5. However, it should be appreciated by those of ordinary skill in the art that the disclosed method 300 may generally be implemented with any work vehicle having any suitable vehicle configuration, with any agricultural implement having any suitable implement configuration, and/or within any system having any suitable system configuration. In addition, although FIG. 6 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 6, at (302), the method 300 includes receiving, with a computing system, LiDAR sensor data associated with return signals detected by a LiDAR sensor configured to emit light-based output signals for reflection off of a field surface of a portion of a field and detect reflections of the light-based output signals as the return signals. For instance, as described above, the computing system 108 may be configured to receive LiDAR sensor data associated with return signals detected by the LiDAR sensor(s) 102. The LiDAR sensor(s) 102, in turn, is configured to emit light-based output signals for reflection off of the field surface of a portion of the field and detect reflections of the light-based output signals as the return signals.

Furthermore, at (304), the method 300 includes receiving, with the computing system, soil moisture sensor data indicative of a soil moisture content of the portion of the field. For instance, as described above, the computing system 108 may be configured to receive soil moisture sensor data from the soil moisture sensor(s) 104. The soil moisture sensor data, in turn, is indicative of the soil moisture content of the portion of the field.

Additionally, at (306), the method 300 includes determining, with the computing system, a soil moisture value for the portion of the field based on the received soil moisture sensor data. For instance, as described above, the computing system 108 may be configured to determine a soil moisture value for the portion of the field based on the received soil moisture sensor data.

Moreover, at (308), the method 300 includes determining, with the computing system, a residue coverage value of the portion of the field based on the determined soil moisture value and the received LiDAR sensor data. For instance, as described above, the computing system 108 may be configured to determine a residue coverage value of the portion of the field based on the determined soil moisture value and the received LiDAR sensor data.

In addition, at (310), the method 300 includes controlling, with the computing system, an operation of a ground-engaging tool of an agricultural implement based on the determined residue coverage value. For instance, as described above, the computing system 108 may be configured to control the operation of one or more ground-engaging tools of the agricultural implement 12, such as the disk blades 50 and/or the shanks 46, based on the determined residue coverage value.

It is to be understood that the steps of the control logic 200 and the method 300 are performed by the computing system 108 upon loading and executing software code or instructions which are tangibly stored on a tangible computer readable medium, such as on a magnetic medium, e.g., a computer hard drive, an optical medium, e.g., an optical disc, solid-state memory, e.g., flash memory, or other storage media known in the art. Thus, any of the functionality performed by the computing system 108 described herein, such as the control logic 200 and the method 300, is implemented in software code or instructions which are tangibly stored on a tangible computer readable medium. The computing system 108 loads the software code or instructions via a direct interface with the computer readable medium or via a wired and/or wireless network. Upon loading and executing such software code or instructions by the computing system 108, the computing system 108 may perform any of the functionality of the computing system 108 described herein, including any steps of the control logic 200 and the method 300 described herein.

The term "software code" or "code" used herein refers to any instructions or set of instructions that influence the operation of a computer or controller. They may exist in a computer-executable form, such as machine code, which is the set of instructions and data directly executed by a computer's central processing unit or by a controller, a human-understandable form, such as source code, which may be compiled in order to be executed by a computer's central processing unit or by a controller, or an intermediate form, such as object code, which is produced by a compiler. As used herein, the term "software code" or "code" also includes any human-understandable computer instructions or set of instructions, e.g., a script, that may be executed on the fly with the aid of an interpreter executed by a computer's central processing unit or by a controller.

This written description uses examples to disclose the technology, including the best mode, and also to enable any person skilled in the art to practice the technology, including making and using any devices or systems and performing any incorporated methods. The patentable scope of the technology is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

The invention claimed is:

1. An agricultural implement, comprising:
a frame;
a ground-engaging tool supported on the frame, the ground-engaging tool configured to engage soil within a field as the agricultural implement travels across the field;
a LIDAR sensor configured to emit light-based output signals for reflection off of a field surface of a portion of the field and detect reflections of the light-based output signals as return signals;
a soil moisture sensor configured to generate soil moisture sensor data indicative of a soil moisture content of the portion of the field; and
a computing system communicatively coupled to the LiDAR sensor and the soil moisture sensor, the computing system configured to:
receive LiDAR sensor data associated with the return signals detected by the LiDAR sensor;
determine a soil moisture value for the portion of the field based on the soil moisture sensor data;
determine a residue coverage value for the portion of the field based on the determined soil moisture value and the received LiDAR sensor data;
control an operation of the ground-engaging tool based on the determined residue coverage value; and
compare the determined residue coverage value to a range, and if the determined residue coverage value falls outside of the range, initiate a control action comprising adjusting a penetration depth of the ground-engaging tool.

2. The agricultural implement of claim 1, wherein, when determining the residue coverage value, the computing system is configured to:
determine a reflectivity value of the output signals off of the soil within the field based on the determined soil moisture content value; and
determine the residue coverage value of the portion of the field based on the determined reflectivity value and the received LiDAR sensor data.

3. The agricultural implement of claim 2, wherein, when determining the residue coverage value, the computing system is configured to:
identify sections of the portion of the field exhibiting the determined reflectivity value; and
identify sections of the portion of the field not exhibiting the determined reflectivity value; and
determine the residue coverage value of the portion of the field based on the identified sections of the portion of the field not exhibiting the determined reflectivity value.

4. The agricultural implement of claim 3, wherein, when determining the residue coverage value, the computing system is configured to:
disregard the identified sections of the portion of the field exhibiting the determined reflectivity value;
determine an amount of the portion of the field corresponding to the identified sections of the portion of the field not exhibiting the determined reflectivity value; and
determine the residue coverage value of the portion of the field based on the determined amount.

5. The agricultural implement of claim 1, wherein the ground-engaging tool comprises a disk blade or a shank.

6. A system for determining residue coverage of a field, the system comprising:
a ground-engaging tool configured to engage soil within the field as an agricultural implement travels across the field;
a LIDAR sensor configured to emit light-based output signals for reflection off of a field surface of a portion of the field and detect reflections of the light-based output signals as return signals;
a soil moisture sensor configured to generate soil moisture sensor data indicative of a soil moisture content of the portion of the field; and
a computing system communicatively coupled to the LiDAR sensor and the soil moisture sensor, the computing system configured to:
receive LiDAR sensor data associated with the return signals detected by the LiDAR sensor;
determine a soil moisture value for the portion of the field based on the soil moisture sensor data;
determine a residue coverage value of the portion of the field based on the determined soil moisture value and the LiDAR sensor data;
control an operation of the ground-engaging tool based on the determined residue coverage value; and
compare the determined residue coverage value to a range, and if the determined residue coverage value falls outside of the range, initiate a control action comprising adjusting a penetration depth of the ground-engaging tool.

7. The system of claim 6, wherein, when determining the residue coverage value, the computing system is configured to:

determine a reflectivity value of the output signals off of soil within the field based on the determined soil moisture content value; and determine the residue coverage value of the portion of the field based on the determined reflectivity value and the received LiDAR sensor data.

8. The system of claim 7, wherein, when determining the residue coverage value, the computing system is configured to:

identify sections of the portion of the field having the determined reflectivity value; and identify sections of the portion of the field not having the determined reflectivity value; and determine the residue coverage value of the portion of the field based on the identified sections of the portion of the field not exhibiting the determined reflectivity value.

9. The system of claim 8, wherein, when determining the residue coverage value, the computing system is configured to:

disregard the identified sections of the portion of the field exhibiting the determined reflectivity value;

determine an amount of the portion of the field corresponding to the identified sections of the portion of the field not exhibiting the determined reflectivity value; and determine the residue coverage value of the portion of the field based on the determined amount.

10. The system of claim 6, wherein the soil moisture sensor comprises a microwave signal-based sensor.

11. The system of claim 6, wherein the ground-engaging tool comprises a disk blade or a shank.

12. The system of claim 6, wherein the control action comprises providing a notification to an operator of an agricultural implement on which the ground-engaging tool is installed indicating that the determined residue coverage value falls outside of the range.

13. A method for determining residue coverage of a field, the method comprising:

receiving, with a computing system, LiDAR sensor data associated with return signals detected by a LiDAR sensor configured to emit light-based output signals for reflection off of a field surface of a portion of the field and detect reflections of the light-based output signals as the return signals;

receiving, with the computing system, soil moisture sensor data indicative of a soil moisture content of the portion of the field;

determining, with the computing system, a soil moisture value for the portion of the field based on the received soil moisture sensor data;

determining, with the computing system, a residue coverage value of the portion of the field based on the determined soil moisture value and the received LiDAR sensor data; and controlling, with the computing system, an operation of a ground-engaging tool of an agricultural implement based on the determined residue coverage value; and comparing, with the computing system, the determined residue coverage value to a range, and if the determined residue coverage value falls outside of the range, initiating, with the computing system, a control action comprising adjusting a penetration depth of the ground-engaging tool.

14. The method of claim 13, wherein determining the residue coverage value comprises:

determining, with the computing system, a reflectivity value of the output signals off of soil within the field based on the determined soil moisture content value; and determining, with the computing system, the residue coverage value of the portion of the field based on the determined reflectivity value and the received LiDAR sensor data.

15. The method of claim 14, wherein determining the residue coverage value comprises:

identifying, with the computing system, sections of the portion of the field exhibiting the determined reflectivity value; and identifying, with the computing system, sections of the portion of the field not exhibiting the determined reflectivity value; and determining, with the computing system, the residue coverage value of the portion of the field based on the identified sections of the portion of the field not exhibiting the determined reflectivity value.

16. The method of claim 15, wherein determining the residue coverage value comprises:

disregarding, with the computing system, the identified sections of the portion of the field exhibiting the determined reflectivity value;

determining, with the computing system, an amount of the portion of the field corresponding to the identified sections of the portion of the field not exhibiting the determined reflectivity value; and determining, with the computing system, the residue coverage value of the portion of the field based on the determined amount.

17. The method of claim 14, wherein the soil moisture sensor data comprises a microwave signal-based sensor data.

* * * * *